(12) United States Patent
Cheminet

(10) Patent No.: US 10,527,561 B2
(45) Date of Patent: Jan. 7, 2020

(54) DEVICE AND METHOD FOR ANALYSIS OF MATERIAL BY NEUTRON INTERROGATION

(71) Applicant: SODERN, Limeil Brevannes (FR)

(72) Inventor: Adrien Cheminet, Vincennes (FR)

(73) Assignee: SODERN, Limeil Brevannes (FR)

( * ) Notice: Subject to any disclaimer, the term of this patent is extended or adjusted under 35 U.S.C. 154(b) by 0 days.

(21) Appl. No.: 16/112,369

(22) Filed: Aug. 24, 2018

(65) Prior Publication Data
US 2019/0094157 A1   Mar. 28, 2019

(51) Int. Cl.
| | |
|---|---|
| *G01N 23/05* | (2006.01) |
| *G01V 5/00* | (2006.01) |
| *G01N 23/20066* | (2018.01) |
| *G01N 23/046* | (2018.01) |
| *G01N 23/20* | (2018.01) |

(52) U.S. Cl.
CPC .......... *G01N 23/05* (2013.01); *G01N 23/046* (2013.01); *G01N 23/20* (2013.01); *G01N 23/20066* (2013.01); *G01V 5/0025* (2013.01); *G01V 5/0069* (2016.11); *G01N 2223/419* (2013.01)

(58) Field of Classification Search
CPC ............ G01N 23/05; G01N 23/20066; G01N 23/046; G01N 2223/419; G01N 23/20; G01V 5/0025; G01V 5/0069
See application file for complete search history.

(56) References Cited

U.S. PATENT DOCUMENTS

| | | | | |
|---|---|---|---|---|
| 6,484,051 | B1* | 11/2002 | Daniel | G01N 23/20 250/363.03 |
| 9,535,016 | B2* | 1/2017 | Xu | G01N 23/20066 |
| 2012/0256094 | A1* | 10/2012 | Pozzi | G01V 5/0091 250/366 |
| 2015/0377804 | A1* | 12/2015 | Arsenault | G01N 23/20066 250/393 |
| 2018/0038967 | A1* | 2/2018 | Li | G01T 1/1603 |

* cited by examiner

*Primary Examiner* — Kiho Kim
(74) *Attorney, Agent, or Firm* — Osha Liang LLP

(57) ABSTRACT

Material analysis device (100) comprising a neutron generator (10) for emitting neutrons towards a material to be analysed in pulsed mode; an alpha particle detector (13) for locating the neutrons emitted in a given solid angle by detecting alpha particles associated with these neutrons; at least one gamma ray detector (14) for measuring energy of gamma photons generated by interaction of the neutrons emitted in the given solid angle with the material to be analysed; at least two Compton cameras (15), each for measuring energy of the gamma photons generated by interaction of the neutrons with the material to be analysed and for calculating an incidence cone of these gamma photos; and an electronic circuit adapted for three-dimensionally mapping the presence of at least one chemical element of interest in the material to be analysed based on data provided by the alpha particle detector (13), the gamma ray detector (14) and the Compton cameras (15).

14 Claims, 5 Drawing Sheets

DEVICE AND METHOD FOR ANALYSIS OF MATERIAL BY NEUTRON INTERROGATION

TECHNICAL FIELD

The present disclosure relates to a device and a method for analysis of material by neutron interrogation. This device and this method are able to detect the presence of certain chemical elements in the material by measuring the radiation emitted by these elements when the material is exposed to a neutron flux. They can be used in particular for detection of explosive substances buried in the ground.

TECHNOLOGICAL BACKGROUND

A known method for analysis of material by neutron interrogation is based on the emission of neutrons towards the material to be analysed, on detection, by a gamma ray detector, of gamma photons emitted during the first interaction of neutrons with the material to be analysed and on detection, by an alpha particle detector, of the alpha particles associated with the emitted neutrons. This method of analysis by detection of associated alpha particles is commonly referred to as the "API" (Associated Particle Imaging) method. The API method not only allows determination of the presence of certain elements, but also three-dimensional localisation of these elements in the material analysed. Such a method is described for example in patent document FR 2945631.

Although this method is generally satisfactory, the gamma ray detector data acquisition time is relatively long, which may be problematic for some applications. This is the case for example of applications in which the material to be analysed and the analysis device move in relation to each other and in which all the data required for the analysis need to be acquired during this movement.

In order to overcome this drawback, a solution would involve increasing the neutron flux emitted to increase the number of interactions with the material. Thus, more data would be collected during an acquisition period and the length of this period could be reduced. However, increasing the neutron flux would require a neutron generator that is more powerful, therefore larger, heavier and consuming more electrical energy. Moreover, by increasing the neutron flux, the surrounding radioactivity would increase and provision would need to be made for thicker shielding to protect the users against this radioactivity. Ultimately, the mass and overall dimensions of the device would be significantly increased, which would represent a disadvantage in applications in which the analysis device is mobile, such as for example applications in which the device is mounted on a vehicle.

Consequently, there is a need for a new type of device for analysis of material by neutron interrogation, making it possible to offset, at least in part, the above-mentioned drawbacks.

GENERAL OVERVIEW

The present disclosure relates to a device for analysis of material by neutron interrogation comprising:
- a neutron generator for emitting neutrons towards a material to be analysed, wherein the neutron generator comprises a neutron tube equipped with an electrical supply enabling the neutron generator to operate in pulsed mode;
- an alpha particle detector allowing location of neutrons emitted at a given solid angle by detecting alpha particles associated with these neutrons;
- at least one gamma ray detector for measuring energy of gamma photons generated by interaction of the neutrons emitted in the given solid angle with the material to be analysed;
- at least two Compton cameras each for measuring energy of gamma photons generated by neutron interaction with the material to be analysed and for calculating an incidence cone of these gamma photons; and
- an electronic circuit adapted for three-dimensionally mapping the presence of at least one chemical element of interest in the material to be analysed based on data provided by the alpha particle detector, the gamma ray detector and the Compton cameras.

The device generally comprises several gamma ray detectors. The alpha particle and gamma ray detectors allow implementation of the API method mentioned above. In other words, the data provided by the alpha particle detector are processed in conjunction with the data provided by the gamma ray detectors in order to locate three-dimensionally, using the API method, the chemical element of interest in the material to be analysed.

At least one of said Compton cameras can also be used to implement the API method. In this case, the data provided by the alpha particle detector are processed in conjunction with the data provided by the gamma ray detectors and by the Compton camera in order to locate three-dimensionally, using the API method, the chemical element of interest in the material to be analysed. In other words, the Compton cameras can be used, in addition to the gamma ray detectors, to collect the data useful for the API method. Increasing the number of detectors allows the data to be collected more rapidly and thus increases the speed at which the API method can be executed.

Furthermore, the two Compton cameras are used for implementation of the so-called "TNA" (Thermal Neutron Analysis) analysis and localisation method described in detail below and for three-dimensional localisation, by stereoscopy or any other equivalent method, of the chemical element of interest in the material to be analysed. The data thus collected prove complementary to those collected using the API method, which allows an increase in the precision and reliability of the analysis.

Hence, in comparison to a device solely employing the API method and in which the number of gamma ray detectors would be increased, the proposed device makes it possible to perform more precise and more reliable mapping.

Furthermore, using only one neutron generator for both the API and TNA methods makes it possible to limit the mass, overall dimensions and electricity consumption of the device, which represents an advantage, particularly in applications in which the analysis device is mobile. In addition, in comparison to the known devices, the neutron flux does not have to be increased. This makes it possible to limit surrounding radioactivity and safeguard users' safety. Such a device therefore allows rapid, reliable and precise analysis of the material, while remaining relatively light and compact. It is therefore particularly well adapted to applications in which the device needs to be mobile.

In some embodiments, the electronic circuit processes the energy measurements provided by the gamma ray detector or at least one of the Compton cameras in order to select the chemical element of interest among the constituent elements of the material to be analysed. This prior selection makes it possible to limit application of the TNA method to certain elements, the presence of which has been verified. This results in shorter processing times. Thus, the speed of the analysis is maintained, despite implementation of the TNA method. Likewise, application of the API method can also be restricted to this or these chemical element(s) of interest to increase the speed of analysis.

Therefore, in some embodiments, the electronic circuit executes a three-dimensional localisation algorithm, more specifically the TNA method localisation algorithm and only the data relating to the chemical element of interest, among the data provided by the Compton cameras, are used as the algorithm input data. In other words, application of the TNA method and localisation by stereoscopy are restricted to one or more previously selected chemical elements of interest.

Likewise, in some embodiments, the electronic circuit executes a three-dimensional localisation algorithm, more specifically the API method localisation algorithm and only the data associated with the chemical element of interest, among the data provided by the alpha particle detector, are used as the algorithm input data. In other words, application of the API method is restricted to one or more previously selected chemical elements of interest. It should be noted that the data of the alpha particle detector do not contain any information concerning the nature of the chemical elements detected. It is the data of the gamma ray detector that contain this type of information. Therefore, in order to select the data associated with the chemical element of interest among the data provided by the alpha particle detector, the data relating to the chemical element of interest are first selected from among the data of the gamma ray detector and the data temporally associated with the data relating to the chemical element of interest of the gamma ray detector are subsequently selected from among the data of the alpha particle detector.

In some embodiments, the material analysis device comprises mechanisms for orienting the Compton cameras. This optimises gamma photon detection by these cameras.

In some embodiments, shielding is arranged around the gamma ray detectors and/or the Compton cameras to limit penetration of neutrons into these detectors and/or cameras. It should be noted however that this shielding remains similar to the shielding employed in the API method, since the neutron flux remains similar. This shielding is not therefore any heavier or bulkier than "conventional" shielding.

In some embodiments, the neutrons emitted by the neutron generator are derived from deuterium-tritium fusion. The energy of these neutrons is in this case around 14 MeV and is suitable for implementation of the TNA method following thermalisation of these neutrons in the surrounding medium consisting of the material to be analysed.

In some embodiments, the device is combined with a displacement system adapted to create a relative movement between the device and the material to be analysed.

In particular, the present disclosure relates to a vehicle equipped with the proposed analysis device. The device may be mounted, for example, on the front of a land vehicle so as to be positioned slightly above the ground. In this case, the analysis of material is performed as the vehicle moves. This allows three-dimensional mapping of the presence of the element(s) of interest in the ground, i.e. in both directions along the surface of the ground and in the direction of the depth of the ground.

The present disclosure also relates to an analysis apparatus comprising the proposed analysis device and a conveyor belt for transporting the material to be analysed, wherein the analysis device is located close to the conveyor and for example, above the latter. The material can be gradually unloaded in this case on to the conveyor belt, which transports it to the analysis device. Owing to the rapidity of analysis of the proposed device, the conveyor belt can operate uninterruptedly and the analysis can be performed continuously.

The present disclosure also relates to a method for analysis of material in which the proposed material analysis device is used. The advantages of this method accrue from the advantages of the analysis device.

Such a method may comprise the following stages:
emission at a moment t of the neutrons towards the material to be analysed, by means of the neutron generator operating in pulsed mode;
data acquisition by the alpha particle detector and the gamma ray detector within a time window $\Delta t$ that follows moment t;
data acquisition by the Compton cameras, within a time window $\Delta t'$ that follows moment $t+\Delta t$; and
processing of the acquired data to produce three-dimensional mapping of the presence of the chemical element of interest in the material to be analysed.

Apart from the aforementioned stages, the proposed method may include one or more of the following stages, considered separately or combined with each other:
before the three-dimensional mapping is performed, the chemical element of interest is selected from among the constituent elements of the material to be analysed by analysing the energy measurements provided by the gamma ray detector or at least one of the Compton cameras,
only the data relating to the chemical element of interest, among the data provided by the Compton cameras, are used as the input data of a three-dimensional localisation algorithm, more specifically the TNA method localisation algorithm,
only the data relating to the chemical element of interest, among the data provided by the alpha particle detector, are used as the input data of a three-dimensional localisation algorithm, more specifically the API method localisation algorithm.

The proposed method can be used for detection of explosive substances and more particularly, substances buried in the ground. In this case, the analysis device is moved over the surface of the ground, for example by means of a land vehicle on which the device is mounted.

The aforementioned characteristics and advantages, in addition to others, will appear on reading the following detailed description. This description refers to the appended drawings.

BRIEF DESCRIPTION OF THE DRAWINGS

The appended drawings are schematic and are not to scale; their purpose is above all to illustrate the principles of the invention.

In these drawings, from one figure (FIG) to another, identical elements (or parts of elements) are identified by the same reference signs.

DETAILED DESCRIPTION OF EXAMPLES

Exemplary embodiments are described in detail below, with reference to the appended drawings. These examples illustrate the characteristics and advantages of the invention. It should be remembered however that the invention is not limited to these examples.

Figure 1A:
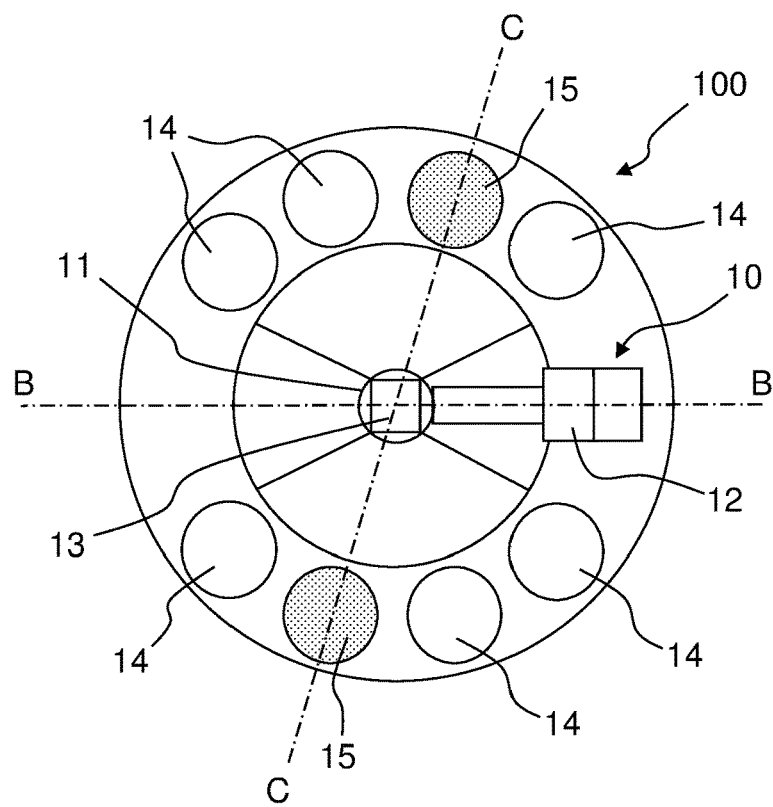
FIG. 1A represents, in a top view, an example of a device for analysis of material by neutron interrogation.
Figure 1B:
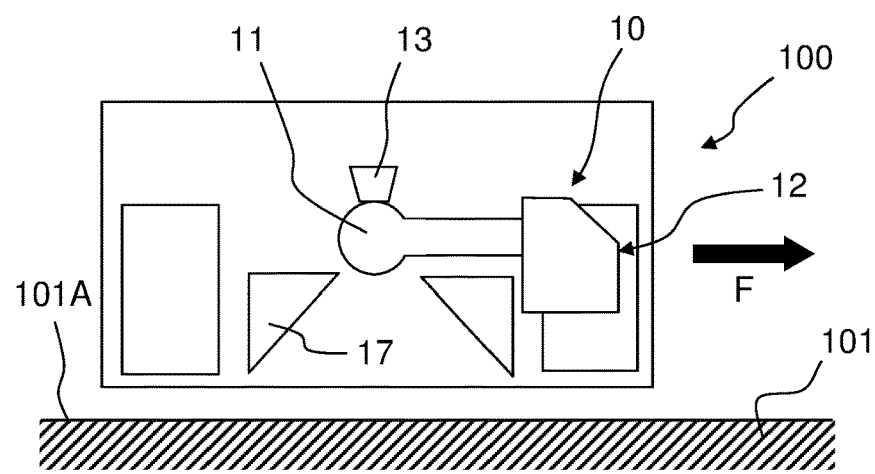
FIG. 1B represents the device in FIG. 1A in a cross-sectional view along the plane B-B.

An example of a material analysis device is illustrated schematically in FIGS. 1A and 1B. This analysis device 100 comprises a neutron generator 10, an alpha particle detector 13, at least one gamma ray detector 14, in this instance six, at least two Compton cameras 15, in this instance two and an electronic processing circuit (not illustrated). The electronic processing circuit can be completely or partly integrated in the detectors 14 and cameras 15 or, on the contrary, be separated from the latter. Shielding 17 can be arranged around the detectors 14 and cameras 15 to restrict neutron penetration in to the latter and therefore reduce the noise in these measuring devices.

The two Compton cameras 15 and the gamma ray detectors 14 can be arranged radially around the neutron source of the neutron generator 10, as shown in FIG. 1A. The number of gamma ray detectors 14 could be increased or reduced according to needs. In particular, it could be increased in order to collect more data during a given acquisition period and thus increase the analysis speed. Likewise, the number of Compton cameras 15 could be increased according to needs.

The device 100 may be arranged over the surface 101A of the material 101 to be analysed, as illustrated in FIG. 1B. It can be mounted on a vehicle (not illustrated) so that the movement of the vehicle moves the device 100 in relation to the material 101 according to the arrow F. The device can be mounted, for example, at the front of a land vehicle and slightly above the ground. In this case, the analysis of material is performed as the vehicle moves.

The neutron generator 10 emits neutrons towards the material 101 to be analysed. It comprises a neutron tube 11 equipped with an electrical supply 12. The electrical supply 12 enables the neutron generator 10 to operate in pulsed mode.

The neutron tube 11 exploits, for example, the fusion reaction between a deuterium nucleus (D or deuton) and a tritium nucleus (T or triton) to generate neutrons, as shown by the following equation: $D+T \rightarrow n+\alpha$.

Figure 2:
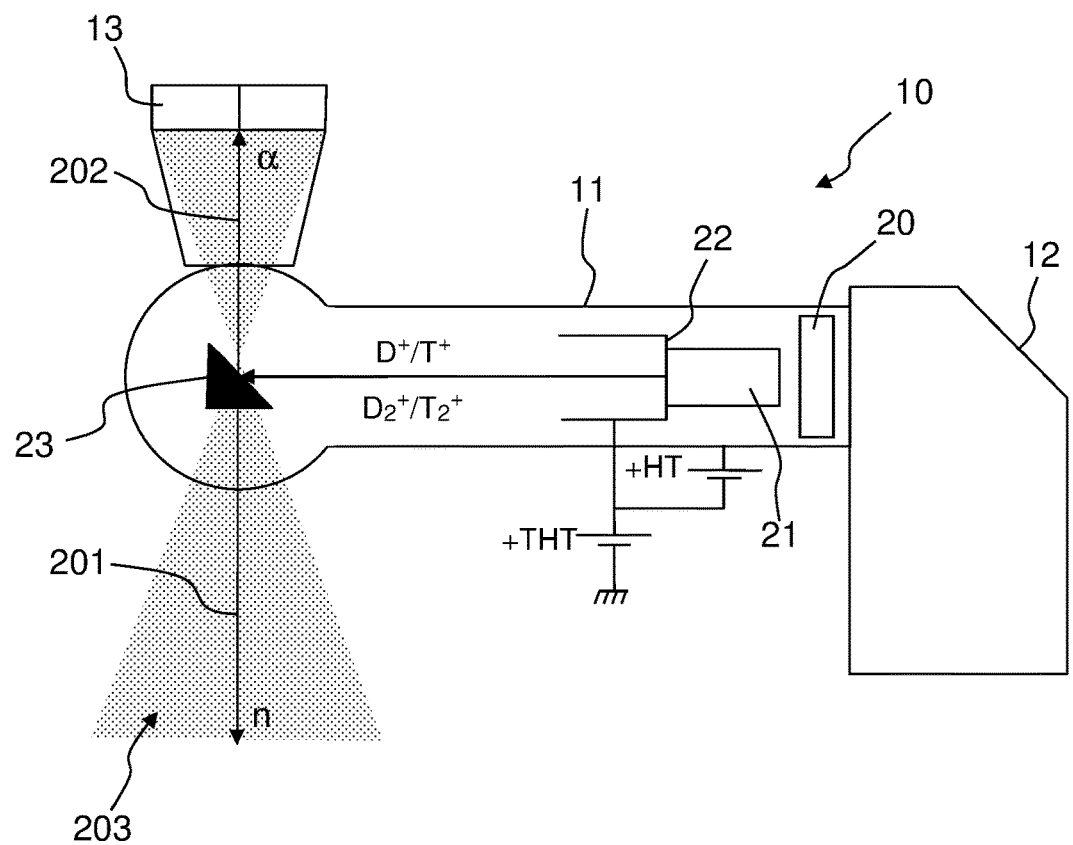
FIG. 2 is a side view of a part of the device in FIGS. 1A and 1B.

Collision between a deuterium nucleus and a tritium nucleus provides a neutron n with an energy of approximately 14 MeV and simultaneously, an alpha particle α with an energy of approximately 3.5 MeV. Consequently and according to the laws of conservation of energy and quantity of motion, a neutron emitted along a path 201 is associated with an alpha particle along a path 202 at 180° to the path 201, as shown in FIG. 2.

A neutron tube 11 may comprise a target 23, a deuterium and/or tritium reservoir 20, an ion source 21 and an accelerating electrode 22. The target 23 is the site of the nuclear reaction between the deuterium and/or tritium nuclei of which it is composed and a beam of incident deuterons and/or tritons (or their molecular form). In order to cause the beam of deutons and/or tritons to collide with the target 23, the beam of deutons and/or tritons is accelerated by an intense electrical field resulting from application of a major voltage difference between the target (cathode) 23 and the accelerating electrode (anode) 22. The beam of deutons and/or tritons is preferably obtained by means of an ion source 22 in which a gaseous mixture of deuterium and tritium originating from the reservoir 20 is ionised. The ions thus generated are subsequently extracted in the acceleration space, forming the beam of deutons and/or tritons.

The neutron tube 11 is equipped with a high voltage electrical supply 12 to generate an intense electrical field resulting from application of a major voltage difference between the target (cathode) 23 and the accelerating electrode (anode) 21. The electrical supply 12 operates in pulsed mode. Pulsed mode means that the electrical supply emits a THT voltage for a pulse duration $\Delta t_0$ and subsequently the electrical supply no longer emits any voltage for a duration $\Delta t_1$. In pulsed mode, this voltage change from 0 to a non-zero THT value is repeated periodically. The THT emitted by the electrical supply causes acceleration of the beam of deutons and/or tritons on the cable and thus emission of neutrons for the pulse duration $\Delta t_0$. Then, no neutrons are emitted for the duration $\Delta t_1$. This is known as operation of the neutron generator in pulsed mode. Neutron emission pulsation can also be obtained by maintaining a direct THT voltage between the target 23 and the accelerating electrode 21. In the latter case, it is the electrical supply of the ion source 21 that operates in pulsed mode, being increased periodically to a HT voltage for a pulse duration $\Delta t_0$ and subsequently zeroed for a duration $\Delta t_1$.

As mentioned above and with reference to FIG. 2, a neutron n emitted towards the material to be analysed 101 along a path 201 is associated with an alpha particle α along a path 202 at 180° to the path 201 of the neutron. Detection of the alpha particle α associated with the neutron n by an alpha particle detector 13 makes it possible to ascertain the path 201 of the neutron n. Thus, the alpha particle detector 13 allows location of the neutrons emitted in a given solid angle 203, by detecting the alpha particles associated with these neutrons. The solid angle 203 is determined by the characteristics of the alpha particle detector 13 and in particular, by its detection area. The detection area of the detector 13 can be spatially discretised in pixels in order to record the position of interaction between the alpha particle and the detector 13. By also knowing the position of the target 23 in relation to the alpha particle detector 13, it is possible to calculate the solid angles of emission of the alpha particle and the neutron associated therewith. The square pixels of the alpha particle detector 13 may typically have dimensions on the order of 5 mm to 25 mm square, which allow solid angles on the order of 0.5% to 2.5% to be obtained compared to $4\pi$ sr for a distance between the target 23 and the alpha particle detector 13 equal to approximately 40 mm.

The alpha particle detector 13 may for example be an Yttrium Aluminium Perovskite (YAP) scintillator, equipped with a set of photomultiplier tubes or a multianode photomultiplier tube. The analysis device 100 could comprise several alpha particle detectors 13.

The neutron emitted by the neutron generator 10 will interact with the material to be analysed 101 by multiple interactions. The first interaction of the neutron with the material 101 will almost instantaneously generate emission of a gamma photon (γ). The energy of this gamma photon will depend on the atom of the material that has interacted with the neutron. Thus, measuring the energy of the gamma photon will allow identification of the nature of the atom.

Furthermore, the temporal coincidences between the alpha particles detected at a moment $t_\alpha$ and the gamma rays resulting from the first interaction detected at a moment $t_\gamma$ are analysed. Knowing the solid angle of emission of the neutron and the speeds of the particles involved (for example 1 cm/ns for particles α of 3.5 MeV, 5 cm/ns for neutrons of 14 MeV and 30 cm/ns for photons γ), the geometric configuration of the system (relative positions of the alpha particle detector and the gamma ray detector with respect to the target 23 emitting neutrons), it is possible to identify a three-dimensional pixel, or voxel, containing the atom that interacted with the neutron in question. This method corresponds to the method of analysis by detection of associated alpha particles, or API method, mentioned above.

The gamma ray detectors 14 allow detection and measurement of the energy of the gamma photons emitted by interaction between the neutrons and the material and thus establishment of the energetic spectrum of these gamma rays. A gamma ray detector may comprise, for example, a scintillating crystal, a photomultiplier and an electronic circuit. The scintillating crystal, or scintillator, may be of the $LaBr_3$, BGO or NaI type, etc. and of sufficient volume to completely arrest incident gamma rays of up to some ten MeV of energy for example. The photomultiplier may be a silicon-based digital component consisting of a matrix in which each pixel is an independent photomultiplier. The electronic circuit can perform a first level of processing of the signal, allowing construction of an energy spectrum.

The resolution of the API method will depend on the resolution in (x, y) of the alpha ray detection matrix and the time "bins"" considered during the test for coincidence (time of flight of the neutron). Thus, each useful coincidence identified is associated with a voxel of the medium. By measuring each time the energy $E_\gamma$ of the gamma photon which is the source of this coincidence, the system determines an energy spectrum that can be used mathematically (deconvolution, spectral decomposition or search for specific lines) to estimate the elemental chemical composition of this voxel and thereby determine the nature of the material analysed.

The data obtained by the API method, which utilises the initial interaction between the neutrons and the material to be analysed, will be supplemented by the data obtained using the so-called "TNA" (Thermal Neutron Analysis) method presented below, which utilises the last interaction between the neutrons and the material.

When a neutron passes through the material to be analysed, it gives up much of its energy as multiple diffusion reactions (elastic or inelastic) occur. This deceleration by a succession of collisions with the nuclei of the material is known as thermalisation. After a certain period of time, typically ranging from a few microseconds to a few hundred microseconds (which is considerable compared to the period of a few nanoseconds elapsing between emission and the first interaction), the neutron has an increasing probability of being absorbed by a nucleus of the medium. When this absorption is accompanied by the prompt emission of a gamma photon, this is called radiative capture.

The gamma photons obtained from the radiative captures are detected by the two Compton cameras 15 in order to obtain information on three-dimensional localisation of the nucleus which is the source of the radiative capture.

Figure 3:
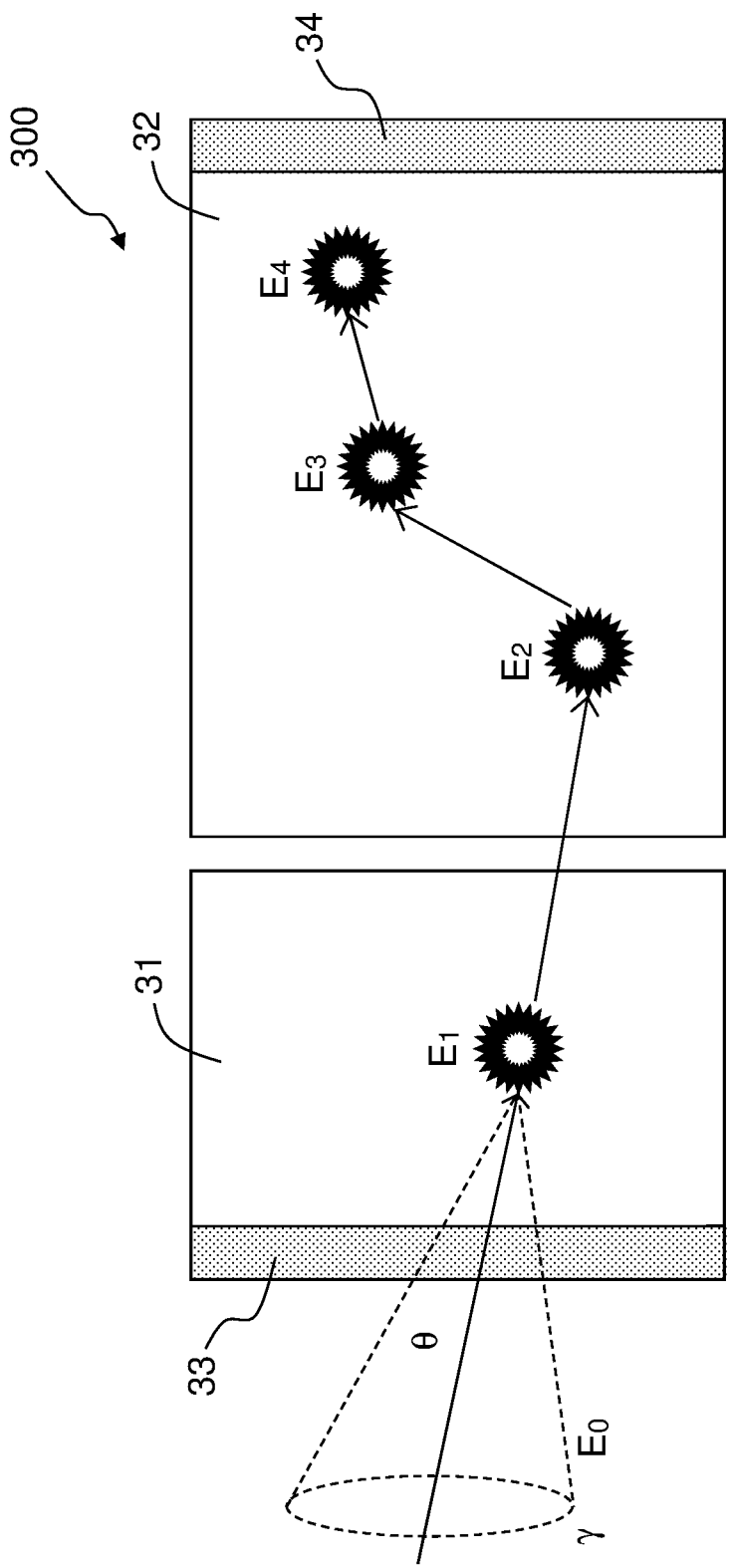
FIG. 3 illustrates the operating principle of a Compton camera.

Generally speaking, a Compton camera comprises a first part known as the diffuser and a second part known as the absorber. An incident photon of a certain energy undergoes initial Compton scattering in the diffuser. Following other interactions, the scattered photon is finally absorbed in the absorber. The operating principle of the Compton cameras 15 is illustrated in the diagram in FIG. 3. The camera 300 may, for example, comprise a first scintillator 31 (composed for example of $LaBr_3$ or BGO), also known as a "scattering crystal", equipped with a photomultiplier 33 and a second scintillator 32, also known as an "absorbent crystal", likewise equipped with a photomultiplier 34. The first and second scintillators 31, 32, respectively from the diffuser and absorber of the camera 300.

When a gamma photon of incident energy $E_0$ enters the scintillator 31, it has a non-zero probability of undergoing Compton scattering. During this scattering, an energy $E_1$ is transferred to the medium. This energy $E_1$ and the position of interaction are measured by the first scintillator 31. If, following the initial Compton scattering, the photon continues its travel to the second scintillator 32, it can then undergo a second Compton scattering during which it gives up an energy $E_2$ and subsequently further Compton scatterings or other mechanisms of interaction such as the photoelectric effect or the creation of pairs until its entire remaining energy has been given up, e.g. it gives up the energies $E_3$, ..., $E_N$, where "N" is a whole number greater than or equal to four in this example. With the position of the second Compton interaction and the total energy deposited by the second photomultiplier 34, it is possible to know the angle θ between the line traversed by the initial incident gamma photon and the direction defined by the two Compton interaction points by means of the following relationship:

$$\cos(\theta) = 1 + M_e \ c^2\left(\frac{1}{E_1} + \frac{1}{E_0 - E_1}\right)$$

Where $M_e$ is the mass of the electron at rest, c is the speed of light in free space and $E_0 = E_1 + E_2 + E_3 + \ldots + E_N$.

Thus, for a photon of energy $E_0$, the Compton camera calculates the half angle θ of the cone defining all possible directions of incidence of this photon. By analysing a sufficient quantity of events corresponding to the same initial energy $E_0$ and if the original source of these photons is relatively "ad hoc", the most probable direction of incidence of these photons of energy $E_0$ can be calculated by integrating all the cones calculated at each event.

Total deposition in the second scintillator 32 of the energy remaining after interaction in the first scintillator 31 is a particularity of the Compton cameras 15, compared with the gamma ray detectors 14 in which the entire initial energy $E_0$ of the gamma photons can be deposited in the single scintillator of the detector 14. In order to ensure that the total energy is deposited in the second scintillator 32, the latter must be of sufficient size (typically on the order of 1 L) to ensure that the entire energy of the gamma photon is deposited, even for very high energies (up to 11 MeV).

Figure 4:
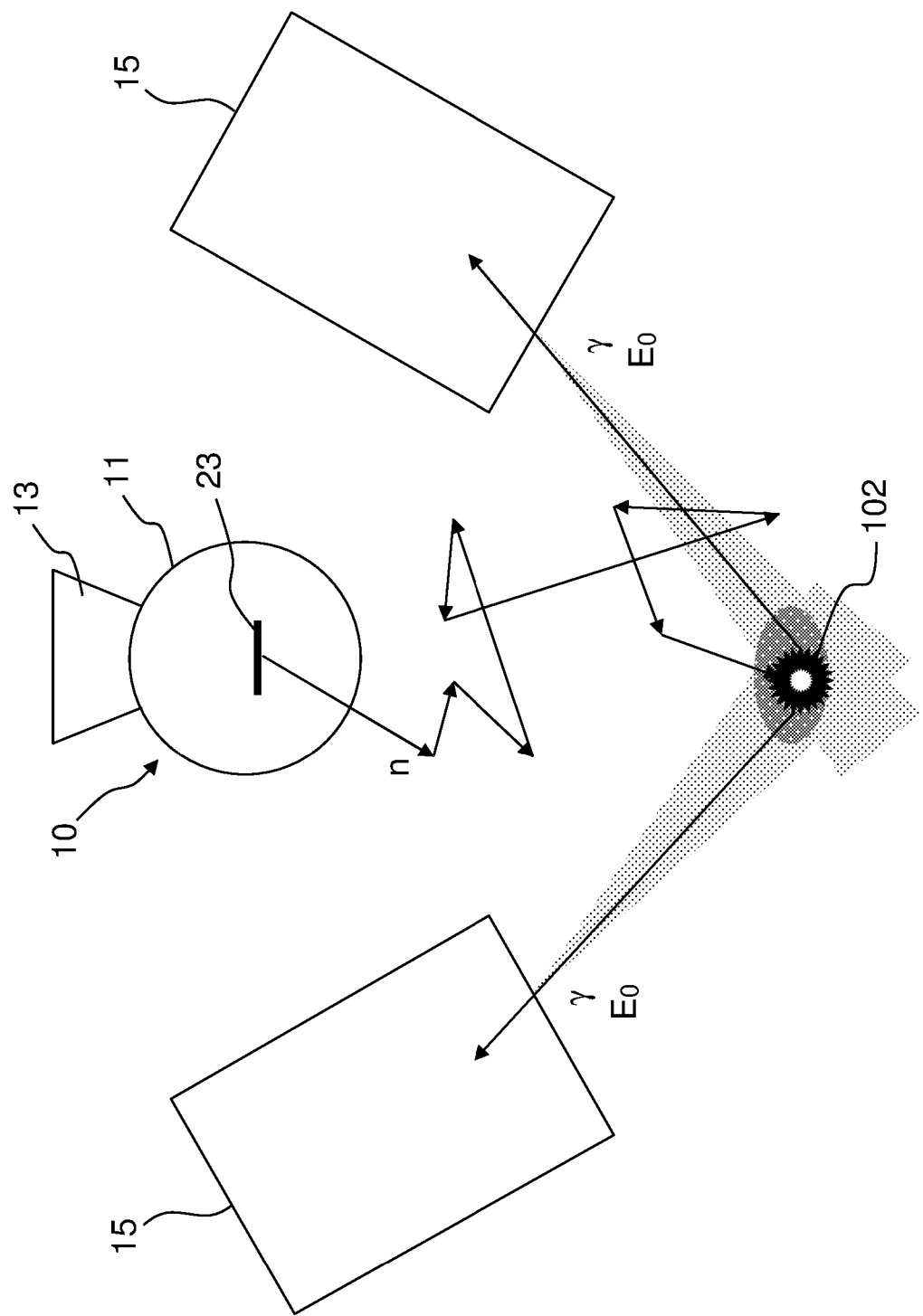
FIG. 4 represents a part of the device in FIG. 1A in a cross-sectional view along the plane C-C.

FIG. 4 illustrates a part of the device in FIG. 1A, in a cross-sectional view along the plane C-C. It schematically represents the neutron generator 10 with the neutron tube 11, the alpha particle detector 13, the target 23 and two Compton cameras 15. Each camera 15 makes it possible, depending on its viewing angle, to know the most probable direction of a gamma ray of energy $E_0$ originating from the interaction between a neutron n emitted by the neutron generator and a same atom 102 of the material 101 to be analysed. The position of the atom 102 in the material to be analysed can be estimated by cross-referencing the data collected by the cameras 15. At least two Compton cameras 15 are required to locate the atom 102 by stereoscopy or any other equivalent method, but a larger number of Compton cameras 15 can be used without going beyond the ambit of the invention. The two Compton cameras 15 can be arranged diametrically opposed to the target 23, as illustrated in FIG. 1A.

Advantageously, only the data relating to gamma photons of a highly specific energy, corresponding to radiative capture by one or more chemical elements of interest among all the constituent elements of the material to be analysed, undergo treatment, so that only these elements of interest are located in the material. By way of an example, nitrogen and/or chlorine isotopes, which are found in the chemical composition of many explosives, may be involved.

Indeed, the localisation algorithms of the API method and above all of the TNA method may be complex and the associated processing times may be longue. Therefore, it is advantageous to restrict the input data of these algorithms to the data relating to the chemical element of interest. For this purpose, a broad energy spectrum representative of the composition of the material 101 can be "rapidly" produced by the gamma ray detectors 14 and/or the Compton cameras 15. This may be an energy spectrum obtained from the initial interaction between the neutrons and the material, or the radiative capture of the neutrons. In particular, the gamma ray detectors 14 are used to produce an energy spectrum, for example for energies corresponding to radiative capture of the neutrons.

The aforementioned localisation algorithms are applied by one or more circuits associated with the detectors 13, 14 and with the cameras 15. These circuits can be completely or partly integrated in the detectors and cameras, or be completely or partly external circuits. These electronic circuits include, for example, microprocessors, computer memories and a set of connections to link the electronic components of the circuits, the detectors 13, 14 and the cameras 15. All these circuits form an electronic circuit within the meaning of the present disclosure.

The angle of orientation of the Compton cameras 15 in relation to the surface of the material to be analysed determines the analysis depth for which the capture gamma ray detection efficiency is optimal. Hence, orientation mechanisms are provided to vary the angle of orientation of the Compton cameras 15 with respect to the surface of the material to be analysed. Such mechanisms allow exploration of the material at different depths.

Owing to their design and in particular, the fact that they include a scintillator and a photomultiplier, Compton cameras 15 can also help to determine the energy spectrum of the gamma photons in the API method. On other words, Compton cameras 15 can not only be used for the TNA method, but also to replace or supplement gamma ray detectors 14 in implementing the API method. In such a case, Compton cameras 15 play a dual role. This makes it possible to reduce the number of gamma ray detectors 14 used. It should be noted however that it is not economically viable to replace all the gamma ray detectors 14 with Compton cameras 15, since the latter are more costly than the gamma ray detectors 14 in this type of device.

Figure 5:
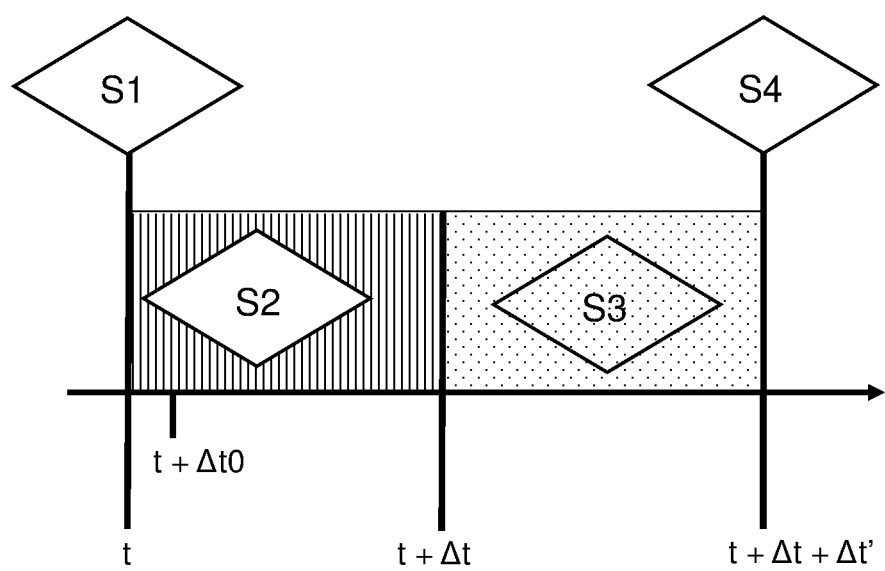
FIG. 5 is a timeline relating to an example of a material analysis method.

An exemplary method for analysis of material by neutron interrogation is illustrated in FIG. 5 in the form of a timeline. This method uses an analysis device 100 as described above. The method includes the following steps:

S1: emission at a moment t for a duration $\Delta t_0$, of neutrons towards the material to be analysed, by means of the neutron generator 10;

S2: acquisition of the data provided by the alpha particle detector 13 and the gamma ray detector 14 within a time window $\Delta t$ that follows moment t;

S3: acquisition of the data provided by the Compton cameras, within a time window $\Delta t'$ that follows moment $t+\Delta t$; and S4: processing of the acquired data to produce three-dimensional mapping of the presence of at least one element of interest in the material to be analysed.

It should be noted that the neutron generator operates in pulsed mode so as not to confuse the gamma rays obtained from the initial interactions (inelastic diffusions) of the neutrons with the material to be analysed with those obtained from the last interactions (radiative captures) of the neutrons with the material to be analysed. Both these types of interaction are characterised by different times: the first occurs a few nanoseconds after emission of the neutrons and the last occurs a few microseconds to a few hundreds of microseconds after emission of the neutrons. Thus, a first time window $\Delta t$ is defined when emission of the neutrons is in progress in order to identify the gamma rays generated by the first interaction and of which the origin can be traced by the associated alpha particle and a second time window $\Delta t'$ is defined in the absence of neutron emission in order to measure the energy of the gamma rays generated by the last interaction.

The embodiments or examples described in the present disclosure are provided by way of illustration and are non-restrictive; a person skilled in the art can easily, in the light of this disclosure, modify these embodiments or examples, or contemplate others, while remaining within the scope of the invention.

Furthermore, the different characteristics of the embodiments or examples described in the present disclosure may be considered separately or combined with each other. When combined, these characteristics may be combined as described above or differently, the invention not being limited to the specific combinations described above. In particular, unless otherwise specified or technically incompatible, a characteristic described in relation to one embodiment or example may be applied in a manner similar to another embodiment or example.

The invention claimed is:

1. Material analysis device comprising:
   a neutron generator for emitting neutrons towards a material to be analysed, wherein the neutron generator comprises a neutron tube equipped with an electrical supply enabling the neutron generator to operate in pulsed mode;
   an alpha particle detector allowing location of neutrons emitted at a given solid angle by detecting alpha particles associated with these neutrons;
   at least one gamma ray detector for measuring energy of gamma photons generated by interaction of the neutrons emitted in the given solid angle with the material to be analysed;
   at least two Compton cameras each for measuring energy of gamma photons generated by neutron interaction with the material to be analysed and for calculating an incidence cone of these gamma photons;
   an electronic circuit adapted for three-dimensionally mapping the presence of at least one chemical element of interest in the material to be analysed based on data provided by the alpha particle detector, the gamma ray detector and the Compton cameras.

2. Material analysis device according to claim 1, wherein the electronic circuit is configured to implement a method of analysis by associated particle imaging, or API method, and a method of thermal neutron analysis, or TNA method, in order to three-dimensionally map the presence of the chemical element(s) of interest.

3. Material analysis device according to claim 1, wherein the electronic circuit processes energy measurements provided by the gamma ray detector and/or at least one of the Compton cameras for selecting the chemical element of interest among elements constituting the material to be analysed.

4. Material analysis device according to claim 1, wherein the electronic circuit executes a three-dimensional localisation algorithm in which only data relating to the chemical element of interest, among data provided by the Compton cameras, are used as algorithm input data.

5. Material analysis device according to claim 1, wherein the electronic circuit executes a three-dimensional localisation algorithm in which only data associated with the chemical element of interest, among data provided by the alpha particle detector, are used as algorithm input data.

6. Material analysis device according to claim 1, combined with a displacement system adapted to create a relative movement between the device and the material to be analysed.

7. Vehicle equipped with a material analysis device according to claim 1.

8. Material analysis method employing a material analysis device according to claim 1.

9. Material analysis method according to claim 8, comprising the following stages:

emission at a moment t of neutrons towards the material to be analysed, by means of the neutron generator operating in pulsed mode;

data acquisition by the alpha particle detector and the gamma ray detector (14) within a time window $\Delta t$ that follows moment t;

data acquisition by the Compton cameras, within a time window $\Delta t'$ that follows moment $t+\Delta t$; and processing of the acquired data to produce three-dimensional mapping of the presence of the chemical element of interest in the material to be analysed.

10. Material analysis method according to claim 9, wherein the data processing implements a method of analysis by associated particle imaging, or API method, and a method of thermal neutron analysis, or TNA method, in order to produce said three-dimensional mapping.

11. Material analysis method according to claim 9, wherein, before the three-dimensional mapping is performed, the chemical element of interest is selected from among elements constituting the material to be analysed by analysing the energy measurements provided by the gamma ray detector and/or at least one of the Compton cameras.

12. Material analysis method according to claim 9, wherein only data relating to the chemical element of interest, among data provided by the Compton cameras, are used as input data of a three-dimensional localisation algorithm.

13. Material analysis method according to claim 9, wherein only data associated with the chemical element of interest, among data provided by the alpha particle detector, are used as input data of a three-dimensional localisation algorithm.

14. Material analysis method according to claim 9, used to detect explosive substances, wherein the chemical element of interest is characteristic of an explosive substance.

* * * * *